United States Patent [19]
Ozaki

[11] 4,201,671
[45] May 6, 1980

[54] CHROMATOGRAPHY METHOD AND APPARATUS

[75] Inventor: Yoshisuke Ozaki, Cambridge, Mass.

[73] Assignee: Massachusetts Institute of Technology, Cambridge, Mass.

[21] Appl. No.: 929,059

[22] Filed: Jul. 28, 1978

[51] Int. Cl.² .............................................. B01D 15/08
[52] U.S. Cl. .................... 210/138; 210/198 C
[58] Field of Search .................... 210/138, 139, 198 C

[56] References Cited

U.S. PATENT DOCUMENTS

| | | | |
|---|---|---|---|
| 3,266,554 | 8/1966 | Brownrigg | 210/198 C |
| 3,341,017 | 9/1967 | Powell | 210/198 C |
| 3,474,031 | 10/1969 | Blondell | 210/138 X |

Primary Examiner—John Adee
Attorney, Agent, or Firm—Arthur A. Smith, Jr.; Paul J. Cook

[57] ABSTRACT

Method and apparatus for effecting thin-layer chromatographic (TLC) analysis including a chamber open at the bottom and adapted to retain a strip of chromatographic material. The chamber is moved in time relation alternatively into and out of a first container of a solution of the material being analyzed to effect alternative irrigation and drying of the strip so that a high resolution of solutes is accomplished on the strip. A secondary reservoir of the solution in a closed container is connected to the first container so as to maintain the solution level in the first container constant.

3 Claims, 1 Drawing Figure

U.S. Patent
May 6, 1980
4,201,671
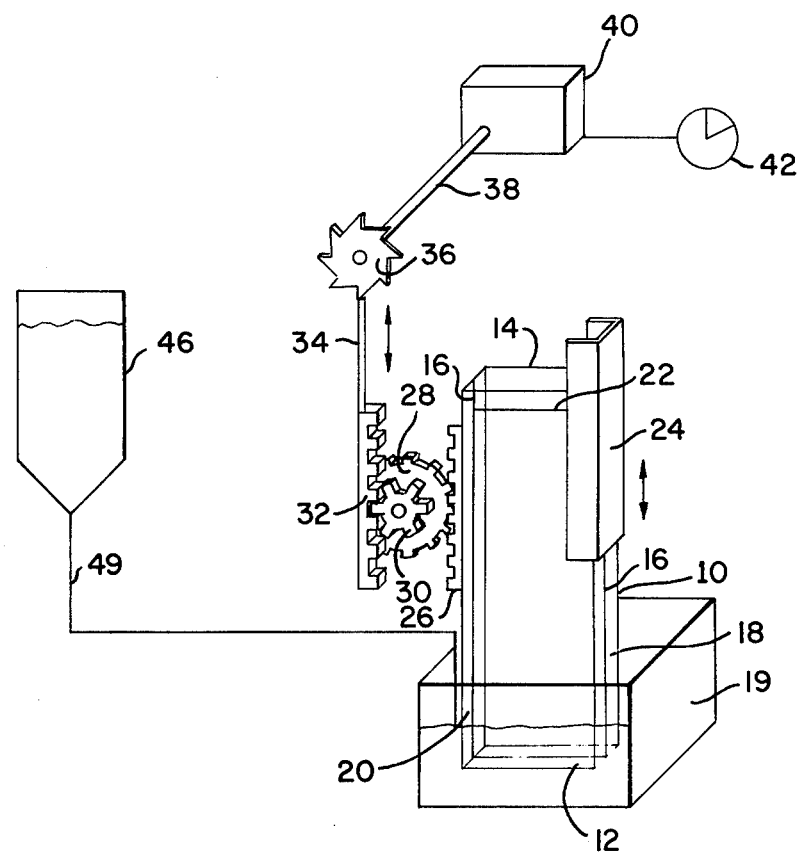

CHROMATOGRAPHY METHOD AND APPARATUS

BACKGROUND OF THE INVENTION

This invention relates to a method and apparatus for conducting chromatographic analysis.

Presently, there are a number of chromatographic methods for isolating organic compounds from complex mixtures of organic compounds in order to identify the type and amounts of the constituents of the mixture. In unidimensional multiple chromatography (UMC), a solution of the organic mixture is resolved with a developing solvent(s) and an absorbent chromatographic material such as alumina and silica gel plate by a normal method wherein the operator does the multiple development by hand. This procedure requires repeated irrigation of the chromatographic material with the solution followed by evaporation of the solvent to leave the solute on the plate. In order to effect separation of mixtures of closely related organic compounds into the constituents of the mixture, long periods of manual work, e.g., up to about 30 hours is required, particularly when a solvent of a weak strength is utilized which comprises effective separation. This procedure is difficult to apply for the routine procedure and is therefore undesirable.

A second method comprises programmed multiple development (PMD) wherein a sandwhich of a chromatographic material formed of silica gel TLC plate is placed in continuous contact with a reservoir of the solution and the solvent is continuously evaporated by exposing the chromatographic material containing the solution to infrared radiation. This method is undesirable since the infrared radiation increases undesirable oxidation and thermal degradation of labile compounds. This, in turn, results in inaccuracy in determining the presence of certain compounds in the sample tested and, if so, the amounts of these compounds in the sample. In addition, heating leads to increased rates of evaporation from the solvent reservoir in which the chromatographic plate is placed. This increased evaporation also leads to inaccuracies since the effect is to reduce the vertical position the solute normally would have on the chromatographic strip. Alternatively, PMD can be conducted by passing a dry inert gas over the chromatographic plate to increase the rate of solvent evaporation. However, uniform evaporation from the plate is difficult with this method which leads to the reduction in a uniform chromatographic resolution of the solute and this method also introduces difficulty in controlling the level of the solvent reservoir.

Alternatively, organic mixtures can be analyzed by gas chromatography. While this method yields efficient discrimination of the constituents of the mixture, it is undesirable for the purpose of the routine application since the required apparatus is extremely expensive.

Accordingly, it would be highly desirable to provide a chromatographic method for analyzing organic mixtures which is at least as accurate as gas chromatographic procedures, does not require manual labor throughout the process and which does not require expensive apparatus.

SUMMARY OF THE INVENTION

In accordance with this invention, a process and apparatus are provided which effect chromatographic separation and isolation of organic compounds from a solution comprising the complex organic mixture (i.e., samples from biological sources) and a solvent for the mixture. Means are provided for alternately introducing and removing a chromatographic plate from a reservoir of the solution which is maintained at a constant vertical level. While in contact with the developing solvent (irrigation), the solvent moves up the chromatographic plate and, as solvent is evaporated, the solute is resolved into a narrow band. When the plate is removed from the solution (drying), the solvent on the plate is evaporated. The cycle is repeated until discernible bands (high resolution) of solutes are formed on the plate. Means are provided for automatically irrigating and drying the plate in timed sequence. The plate is positioned in an open chamber so that solvent evaporation therefrom is continuous without the need for heating or the use of a gas stream. The vertical level of the solution in a first container positioned below the chamber containing the strip is maintained at a constant level by means of a second closed reservoir of the solution which flows by gravity into the first container.

BRIEF DESCRIPTION OF THE DRAWINGS

FIG. 1 is a perspective view of one embodiment of the apparatus of this invention.

DETAILED DESCRIPTION OF PREFERRED EMBODIMENTS

This invention provides the level of accuracy in chromatographic analysis which is presently available only by expensive gas chromatography procedures. In the process of this invention, the solute is concentrated into a narrow band on the chromatographic plate because of the alternate irrigation and drying steps. During each drying step, when the chromatographic strip is lifted from contact with the solution, the unevaporated solvent in the strip descends by gravity to the bottom of the strip and the solute at the upper portion of the solute spot (i.e., leading edge) on the strip moves downward at a faster rate than the solute at the lower portion (i.e., trailing edge) of the solute spot because of the existence of the concentration gradient and the differential velocity of developing solvent relative to the stationary phase (absorbent), i.e., the volatility of a developing solvent is much higher at above the solute spot on the stationary phase than at the lower portion, and since the gravitational force increases the saturation of the lower stationary phase, the solute at the lower edge is much less mobile than the solute at the upper edge (leading edge). Conversely, during the irrigation steps, when the strip is contacted with the solution, the solute spot is moved upward, but the lower portion of the spot moves upward at a faster rate than the upper portion of the spot, i.e., the trailing edge of the solute spot moves a distance farther to the Rf, times the width of the spot, before the leading edge starts to move. In this manner, the repeated and alternating irrigation and drying steps cause the solute in a developing solvent to concentrate into narrow bands on the plate at heights (i.e., Rf) on the plate which correspond to the mobility of the solute.

The time period for drying is such as to permit substantially all of the solvent to evaporate from the chromatographic plate so that during subsequent irrigation, the solute mobilized by the new solvent on the plate can be resolved with a high efficiency. Each irrigation step is conducted for a time to permit the solvent to move upwardly on the plate past the solute spot or band so that solute in solution can be deposited on or near the spot upon evaporation of the solvent from the plate. The particular time for irrigation and drying will depend upon the nature of the solvent and the nature of the solute. Generally, typical drying times are between about 1 min and 15 min and generally typical irrigation times are between about 10 min and 30 min. Generally, the total time to attain chromatographic separation is about 2 to 24 hours with longer times being required for weak solvent and/or for systems utilizing a solvent having a relatively low evaporation rate.

The apparatus of this invention includes a chamber having an open bottom and, preferably an open top, the interior of which is provided with means for positioning and retaining one or more chromatographic strips or plates within the interior of the chamber. Means for raising and lowering the chamber are attached to the chamber so that it can be lifted from or lowered into a first container of a solvent system positioned below the chamber. A second reservoir is provided for housing the solvent being tested which comprises a closed container having a conduit leading into the first container, thereby permitting continuous automatic leveling of the liquid in the first container. The means for moving the chamber comprises a motor having a timing means which regulates start-up, speed and shut-down of the motor. Any equivalent means also can be employed (for example, a solenoid provided with a timer).

Referring to the FIGURE, a chamber 10 having an open bottom 12 and an open top 14 includes slots 16 along the inside surfaces of the sides 18 and 20 into which can be positioned a chromatographic strip 22 formed of paper, alumina, cellulose, silica-gel or the like. The chamber 10 is positioned within a fixed slot 24 so that the chamber's movement can be guided. A gear track 26 is attached to the side 20 of chamber 10 and cooperates with gear 28. Gear 28 and gear 30 are positioned on a common shaft and gear 30 cooperates with gear track 32. Gear track 32 is attached to shaft 34 which cooperates with cam 36. Cam 36 is mounted on motor shaft 38 of motor 40 which, in turn, is regulated by timer 42. A secondary closed reservoir 44 solution is connected to the container 46 through conduit 48.

In operation, irrigation of the chromatographic strip 22 by reservoir 19 is effected by raising shaft 34 and gear track 32 by rotating cam 36. Any suitable spring means (not shown) effects the desired movement. The gears 30 and 28 are rotated to cause gear track 26 and chamber 10 to move downward. Any desired ratio for gears 30 and 28 can be utilized such as 1:2 or 1:3. Drying of the strip 22 is effected when rotation of the cam 36 causes shaft 34 and gear track 32 to move downward. Alternately, the reservoir 19 can be raised and lowered.

The following example illustrates the present invention and is not intended to limit the same.

EXAMPLE I

This example illustrates the isolation of melatonin from biological sources (tissues and urine).

The administration of melatonin, an indolic hormone synthesized in the mammalian pineal organ, inhibits the growth and functional activity of the rat ovary; for example, it delays vaginal opening, reduces ovary weight, depresses the incidence of vaginal smears showing estrous cytology, and suppresses the secretion of luteinizing hormone.

The rate at which pineal organs synthesize and secrete melatonin has been shown to vary with a characteristic 24 hour rhythm that is well synchronized with the environmental photo-period. Melatonin production and release are, in all species examined, greatest during the daily dark period, falling precipitously with the onset of the light period. Normally, this circadian rhythm is synchronized by nerve impulses generated by light acting on the retinas and transmitted to the pineal via norepinephrine released from its sympathetic nerves. Several of the enzymes required for melatonin biosynthesis have also been shown to be influenced by circulating hormones and to exhibit rhythmic changes that parallel the estrous cycle. Studies described in this report show that melatonin secretion in untreated adult rats also varies with the phase of the estrous cycle and that it is diminished by gonadal steroid hormones.

Female Sprague-Dawley rats (Charles River Laboratories, Wilming, Mass.), caged in groups of three to five, were maintained at temperatures of $23° \pm 2°$ in a room lit by Vita-Lite (Duro-Test Corp., North Bergen, N.J.) at an intensity of 300 $\mu W/cm^2$ at the level of the animals; lights were on between 8 a.m. and 8 p.m. The animals were left undisturbed for at least 7 days before use in an experiment. In studies on estrous rhythms, vaginal smears were performed daily, and only rats showing at least three consecutive 4-day cycles were used. In studies on urinary melatonin and norepinephrine, urine was collected from 60-day-old rats between 8 p.m. and 8 a.m. (the period during which at least 80% of the total daily melatonin output is secreted) for at least 12 consecutive days; the rats were housed individually in metabolic cages ($22.5 \times 22.5 \times 27.5$ cm; Acme Metal Products, Chicago, Ill.). In studies on the fate of circulating melatonin, 60-day-old rats received a melatonin injection (250 ng in corn oil, subcutaneously) between 7:30 and 8 p.m. daily for 4 days, and their overnight urine specimens were collected for melatonin assay; daily vaginal smears were also taken and examined. In studies on the effects of castration and exogenous gonadal hormones (estrogen and progesterone), we used 100-day-old rats that had been bilaterally ovariectomized at 40 days of age. The animals were decapitated at 2 a.m. (i.e., 6 hours after the onset of darkness); their pineals and serum samples, which were obtained from trunk blood, were taken for melatonin assays.

Trunk blood from individual animals was collected in $16 \times 100$ mm glass tubes; sera were separated by centrifugation. Immediately after the rats were decapitated, their heads were placed in an ice slurry, and the pineals were removed and frozen in glass homogenizers on dry ice. Each 15 hour urine sample was collected in a 25 ml flask containing 1 ml of 1 M HCl and 20 mg of sodium metabisulfate, its volume was measured, and it was centrifuged at $3000 \times$ g for 10 min. The resulting supernatant fluid was frozen and stored at $-20°$ prior to assay.

The melatonin in urine was extracted into an equal volume of chloroform and isolated by use of a unidimensional multiple-chromatographic procedure described below. After centrifugation at $500 \times$ g, the aqueous phase was transferred to a $16 \times 100$ mm glass tube and its norepinephrine (and epinephrine) content was extracted and assayed. The remaining organic phase was washed successively with 4 ml of 1% sodium bicarbonate solution and 4 ml of deionized water; it was evaporated to dryness under a stream of nitrogen. The dried residue was dissolved in 100 $\mu l$ of absolute ethanol and applied to a thin-layer chromatographic plate ($20 \times 20$ cm silica gel-coated Quantum Linear-Q plate;

Quantum Industries, Fairfield, N.J.) that had been treated with ethanol/ascorbate solution (1 g of ascorbate per 100 ml of absolute ethanol). The plates were developed by ascending multiple chromatography: each plate was developed to 60 mm, and then dried and developed again a total of eight times within a period of approximately 3 hours, using pure chloroform as solvent. A 5 mm segment corresponding to the location of authentic melatonin (chromatographed concurrently) was eluted from each plate with 1 ml of absolute methanol. The eluate was filtered through a phase-separating filter (Brinkman Instruments Inc., Westbury, NY) and evaporated to dryness under a stream of nitrogen. The dried residue was dissolved in 1 ml of 10 mM Tris buffer (pH 7.4), and duplicate aliquots (100–400 μl) were subjected to radioimmunoassay. The recovery of added melatonin (1 ng) by this procedure was 70–80%.

The melatonin in serum was extracted into 3 volumes of chloroform; this organic extract was washed successively with sodium bicarbonate solution and water, after which the organic phase was evaporated to dryness, and the dried residue was dissolved in 100 μl of absolute ethanol. The melatonin was then isolated by use of the unidimensional multiple-chromatographic method and assayed by radioimmunoassay as described above. The recovery of added melatonin from sera also averaged 70–80%.

The melatonin in pineals was extracted into chloroform from 0.1 M HCl homogenates; after being washed similarly, it was reextracted into Tris buffer in the presence of excess η-heptane and subjected to radioimmunoassay.

From the urine samples that had previously been subjected to extraction (of melatonin) with chloroform, norepinephrine and epinephrine were adsorbed onto alumina. The acetic acid eluates were analyzed fluorimetrically for the catecholamines.

The radioimmunoassay for melatonin was performed as described by Levine and Riceberg, Res. Commun. Chem. Pathol. Pharmacol, 10, 693–702. The sensitivity of this assay was $5 \times 10^{-2}$ pmol per sample; the intra-assay and inter-assay coefficients of variation for 100-pg samples were 3 and 4% respectively. The melatonin contents of some extracts was also estimated by using a bioassay based on the dermal melanoplore response of larval anurans to the melatonin in their bathing medium.

Pooled extracts containing sufficient quantities of melatonin for both radioimmunoassay and bioassay were also subjected to an authentication procedure that used the open-chamber programmed-multiple-development device of this invention, which accomplishes multiple development through a clock-operated rack-and-pinion mechanism. In accordance with a predetermined program, it allows the solvent (e.g., chloroform) front to advance repeatedly to 120 mm. Between periods of development, the thin-layer chromatographic plate and its chamber are automatically withdrawn from the developing solvent and the solvent is allowed to evaporate from the silica gel surface. The system affords a distinctive resolution of melatonin; a mixture of melatonin and N-acetyltryptamine (compounds virtually inseparable by simple chromatographic methods) applied to a thin-layer chromatographic plate and subjected to this procedure is resolved in 24 hours as two discrete bands 10 mm apart. When the constituents of a urine extract were distributed on a chromatogram in this manner and 5 mm segments were eluted and submitted to both radioimmunoassay and bioassay, virtually all of the material detectable by bioassay, and most detected by immunoassay, exhibited mobility identical to that of authentic melatonin.

Data were evaluated by analysis of variance and covariance for repeated measurements, linear correlation and regression analysis, Bartlett's test for homogeneity of variances, and t-test; these analyses were performed by use of an IBM S/370 model 168 computer and the Biomedical Computer Programs (revised in Aug., 1976) developed at the Health Science Computing Facility, U.C.L.A., under N.I.H. Special Research Resources Grant PR-3.

In each of two experiments, individual nocturnal urine samples were collected for 12 consecutive days from six rats known to undergo regular 4-day vaginal estrous cycles. Vaginal smears taken daily and concurrently were identified as proestrous, estrous, metestrous, or diestrous, and data for each phase for each animal were pooled. (The data for each phase usually consisted of three individual samples collected on three different days.) Highly significant phasic variations in melatonin excretion were consistently observed ($P<0.001$ by analysis of variance). A 30–50% fall in melatonin excretion was consistently observed for each animal between metestrus or diestrus and proestrus; ($P<0.001$ by t-test); estrous values were intermediate. The reduction in melatonin excretion during proestrus was consistent with the reduction in melatonin-synthesizing activity noted previously.

The levels of norepinephrine (but not epinephrine) in the urine of individual rats exhibited similar phasic variations ($P<0.05$ by analysis of variance); paralleling the reduction in melatonin excretion, norepinephrine levels were also lowest on the night of proestrus ($P<0.005$ compared with metestrus of $P<0.01$ compared with diestrus, by t-test).

The relationship between the melatonin and norepinephrine contents of individual samples was apparently linear, i.e., the slope of the line generated from data of urine collected during all phases was highly significant at $P<0.001$, by analysis of variance. Its correlation coefficient (0.430) was significantly different from zero at $P<0.01$. If the data were subdivided, and those from metestrus-diestrus and proestrus-estrus plotted separately, it was apparent that uninary melatonin and norepinephrine were significantly correlated only for the former ($P<0.01$ by analysis of variance; correlation coefficient=0.434, $P<0.01$). The slope for the least-squares line representing proestrous-estrous phases was insignificant ($P<0.1$ by analysis of variance). This finding suggests that factors other than norepinephrine—presumably circulating gonadal steroids—significantly affect melatonin secretion during these phases.

Nocternal sera from 100-day-old rats, oophorectomized 60 days earlier, contained significantly higher melatonin concentrations than those from sham-operated animals ($P<0.01$). Administration of either 17 β-estradiol benzoate (50 μg/kg, subcutaneously, 55.31, and 7 hours prior to decapitation) or progesterone (1 mg/kp, subcutaneously, 7 hours prior to decapitation) partially suppressed this elevation; administration of both ovarion hormones fully suppressed it ($P<0.01$). Neither oophorectomy nor gonadal steroid administration significantly altered pineal melatonin levels.

To determine whether the fall in urinary melatonin occurring during proestrus represented changes in the metabolism or renal clearance of the circulating indole (as opposed to a reduction in its rate of secretion), the animals were given a fixed dose of melatonin (250 ng/day in corn oil, subcutaneously at various phases of the estrous cycle and determined its effect on urinary melatonin levels. Total melatonin excretion among groups of rats receiving a single dose of melatonin on one of the 4 days of the estrous cycle were: proestrus, $3.20 \pm 0.30$ ng/12 hours (mean$\pm$SEM); estrus, $3.24 \pm 0.30$ ng/12 hours; metestrus, $3.43 \pm 0.35$ ng/12 hours; and diestrus, $2.47 \pm 0.42$ ng/12 hours. If urinary melatonin levels resulting from the endogenous hormone are subtracted from these values, there are no day-related differences in the increments of urinary melatonin caused by this melatonin dose. Hence, it seems likely that the cyclic changes in urinary melatonin reflect variations in the hormone's secretion and not in its peripheral metabolism or renal clearance.

I claim:

1. Apparatus for effecting thin-layer chromatographic separation of mixtures of organic material in a solvent solution which comprises means for alternately and repeatedly introducing and removing a chromatographic plate from a reservoir of the solution in a container, means for maintaining said reservoir within said container at a constant vertical level, and means to control the time the plate is in contact with the reservoir to permit the solvent to move upwardly on the plate past a spot previously deposited on the plate and to control the time the plate is removed from the reservoir to permit substantially all the solvent on the plate to evaporate.

2. The apparatus of claim 1 wherein a container for said reservoir is alternately lifted and lowered.

3. The apparatus of claim 1 wherein the plate is alternately lifted and lowered into and away from contact with said reservoir.

* * * * *